United States Patent

Obayashi et al.

[11] 3,953,173
[45] Apr. 27, 1976

[54] GAS-SENSOR ELEMENT AND METHOD FOR DETECTING OXIDIZABLE GAS

[75] Inventors: Hidehito Obayashi; Tetsuo Gejyo; Tetsuichi Kudo, all of Tokyo, Japan

[73] Assignee: Hitachi, Ltd., Japan

[22] Filed: July 5, 1973

[21] Appl. No.: 376,717

[30] Foreign Application Priority Data
July 8, 1972 Japan.............................. 47-68309
Apr. 27, 1973 Japan.............................. 48-47302

[52] U.S. Cl........................... 23/232 E; 23/254 E; 338/34; 73/27 R
[51] Int. Cl.²................ G01N 27/04; H01C 13/00
[58] Field of Search................ 23/232 E, 254 E; 73/27 R; 338/34; 324/71 SN

[56] References Cited
UNITED STATES PATENTS

| | | | |
|---|---|---|---|
| 3,609,732 | 9/1971 | Kashara............................ | 23/254 E |
| 3,625,756 | 12/1971 | Taguchi............................ | 23/254 E |
| 3,695,848 | 10/1972 | Taguchi............................ | 73/27 R |
| 3,732,519 | 5/1973 | Taguchi............................ | 338/34 |
| 3,793,605 | 2/1974 | Fehlner............................ | 338/34 |

OTHER PUBLICATIONS
Chem. Abstracts, Vol. 74: 35695K (1971).
Chem. Abstracts, Vol. 70: 62070d (1969).
Chem. Abstracts, Vol. 65: 6697f (1966).
J. Inorg. Nucl. Chem., Vol. 27, pp. 2683–2684 (1965).

*Primary Examiner*—Morris O. Wolk
*Assistant Examiner*—Timothy W. Hagan
*Attorney, Agent, or Firm*—Craig & Antonelli

[57] ABSTRACT

A gas-sensor element for detecting oxidizable gases and vapors such as alcohols for carbon monoxide, which is characterized by comprising a complex metal oxide having the $K_2MgF_4$-type crystal structure and represented by the general formula $A_{2-x}A'_xBO_{4-\delta}$, wherein A is at least one element selected from the group consisting of rare earth elements of the atomic numbers from 57 to 71, yttrium, and hafnium, A' is at least one element selected from the group consisting of alkaline earth metals and lithium, B is at least one element selected from the group consisting of transition elements of the atomic numbers from 21 to 30, 0 is oxygen, x is in the range of $0 \leq x \leq 2$, and $\delta$ is a nonstoichiometric parameter.

38 Claims, 7 Drawing Figures

GAS-SENSOR ELEMENT AND METHOD FOR DETECTING OXIDIZABLE GAS

BACKGROUND OF THE INVENTION

This invention relates to a sensor element for detecting trace amounts of gaseous oxidizable substances such as alcohols, aldehydes, hydrocarbons, carboxylic acids, amines, carbon monoxide, and hydrogen contained in the atmosphere, exhaust gases and the breath and a method for detecting the oxidizable gas.

For detecting the above-noted gaseous substances in the atmosphere, an exhaust gas, the breath, etc., there have hitherto been known various methods such as gas chromatography, chemical analysis, and nondispersive infrared absorption spectroscopy. These detecting methods, however, have such disadvantages as complexity of the device, requirement of skill for the analytical procedure, lack of instantaneousness owing to the time-consuming procedure, unsuitableness for a sample gas rapidly changing in composition owing to long intervals between samplings, and expensiveness of the device.

On the other hand, among devices which make use of a semiconductor as the sensing element, there has been known an ethanol sensor comprising n-type tin oxide. This element is evaluatd as having been improved to some degree in the above-said disadvantages. However, when the said substance is used in detecting ethanol, the ethanol is adsorbed on the semiconductor surface. Consequently, although the element is effective for the first sensing operation, it is unsuitable for a continuous use. In case it is to be used repeatedly, it must be heated each time at a temperature of 350°C. or higher to desorb the ethanol. The element has additional disadvantages in that it is incapable of quantitative sensing because of failure in responding proportionally to the ethanol concentration and that in order to compensate a large temperature coefficient of its electric resistance, the external circuit connecting to the sensing element becomes complicated.

SUMMARY OF THE INVENTION

This invention relates to an inexpensive sensor element which may detect by means of a simple device instantaneously and quantitatively trace amounts of oxidizable gases contained in the atmosphere, exhaust gases, and the breath and which has a stable response performance.

This invention provides a gas-sensor element characterized by comprising a complex metal oxide which has substantially the same crystal structure as that of a $K_2MgF_4$-type compound and is represented by the general formula $A_{2-x}A'_xBO_{4-\delta}$, wherein A is at least one element selected from the group consisting of rare earth elements of the atomic numbers from 57 to 71, yttrium, and hafnium, A' is at least one element selected from the group consisting of alkaline earth metals and lithium, B is at least one element selected from the group consisting of transition elements of the atomic numbers from 21 to 30, 0 is oxygen, $x$ is in the range of $0 \leq x \leq 2$, and $\delta$ is a nonstoichiometric parameter.

DESCRIPTION OF THE PREFERRED EMBODIMENTS

Contrary to the ordinary oxides, the complex metal oxide having a $K_2MgF_4$-type crystal structure and represented by the general formula $A_{2-x}A'_xBO_{4-\delta}$ (hereinafter referred to simply as complex oxide and the number of oxygen atoms is expressed simply as 4, $\delta$ being omitted from the expression unless specially needed) has an extremely high electric conductivity even at room temperature.

Figure 1:
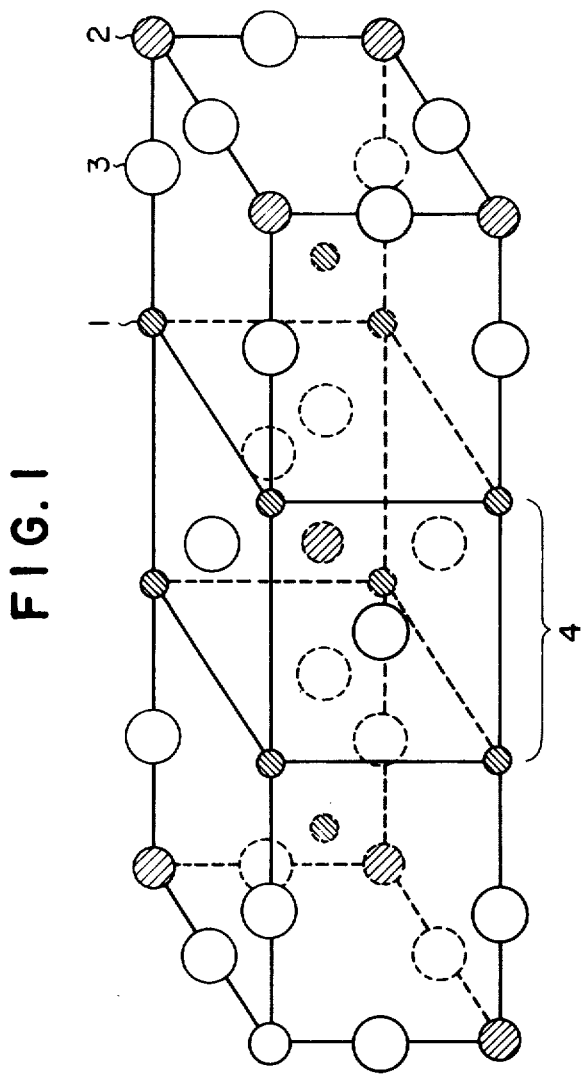
FIG. 1 is a drawing illustrating a unit cell of the crystal of a complex oxide having a $K_2MgF_4$-type crystal structure.
Figure 2:
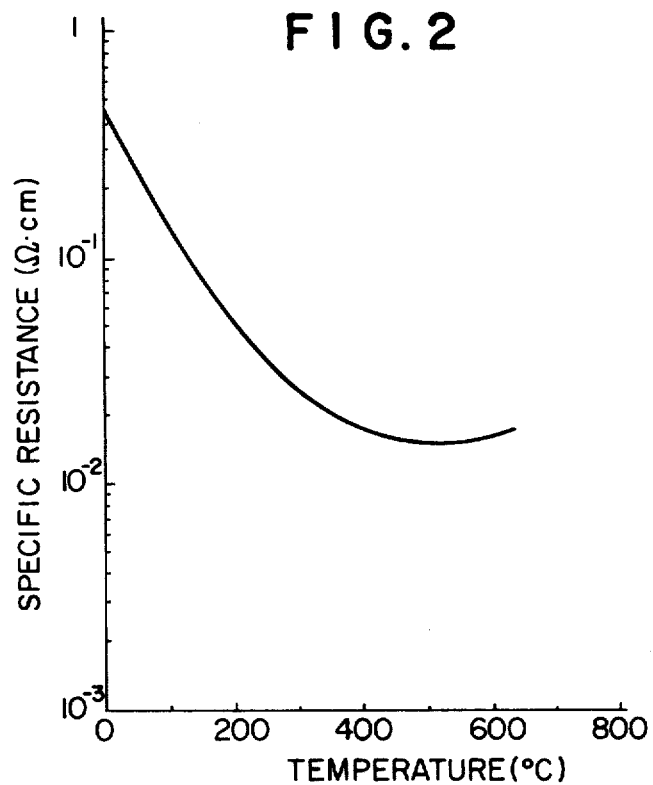
FIG. 2 is a diagram representing the change in specific resistance of a sensor element comprising $Nd_{1.5}Sr_{0.5}NiO_4$ relative to the temperature change.
Figure 3:
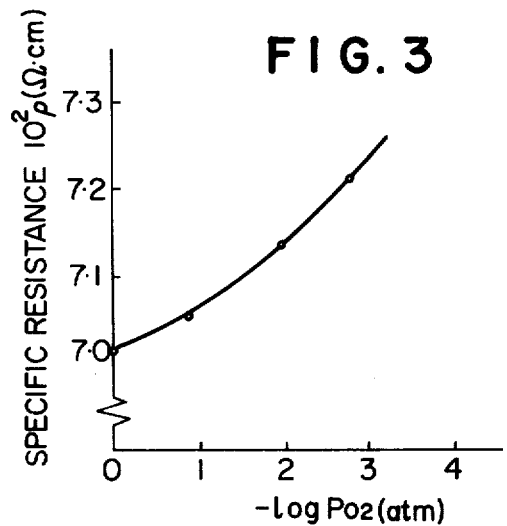
FIG. 3 is a characteristic diagram representing the relationship between specific resistance of a sensor element comprising $La_{1.4}Sr_{0.6}NiO_4$ and the change in oxygen partial pressure.

The $K_2MgF_4$-type crystal structure is shown in FIG. 1. The FIGS. 1, 2, and 3 represent the elements A or A', B, and oxygen, respectively. It is seen that in the unit cell shown in FIG. 1, a domain indicated by 4 has the same structure as the perovskite-type crystal structure. Thus, the complex oxide having a $K_2MgF_4$-type structure may be characterized as a complex oxide having a multi-layered sandwich structure composed of layers of two-dimensionally developed perovskite-type crystal lattice and interposed layers of other type crystal lattice. To such a crystal structure may be ascribable the above-said high electric conductivity of the complex oxide. There are several literature references concerning the mechanism of electric conductivity of these oxides [e.g., R. R. Heikes et al., Physica, 30, 1600 (1964); I. H. van Santen et al., ibid., 16, 599 (1950); I. B. Goodenough et al., Landolt-Börnstein, IV/4a, 126 (1970)]. The mechanism may be interpreted as follows: compensation of the charge resulting from substitution of a part of A with A' is undertaken by the element B when B is of a multiple valency element, and thus the electric conduction occurs by the mechanism in which electrons move through the three-dimensional network of B-O-B.

For synthesizing these complex oxides, there are several methods such as, for example, a method of synthesizing from oxides, a method of synthesizing from salts such as carbonates, nitrates, and acetates, a method in which the oxygen partial pressure in an atmospheric gas is controlled, and a method which makes use of an alkaline metal carbonate as a flux.

In synthesizing from oxides, predetermined amounts of the component oxides are weighed out, ground finely, and mixed thoroughly. The sample is obtained by sintering the oxide mixture at between 1,000° to 1,400° C. for 2 to 24 hours. During sintering, the oxygen partial pressure is controlled in the following manner. A tolerance factor $t$, as defined similarly to the case where the factor is applied to the perovskite structure, is taken into account for each complex oxide. According to the magnitude of the factor, a reducing or oxidizing atmosphere is employed. The oxygen partial pressure $Po_2$ is suitably selected from the range of $10^{-20}$ to 1 atmosphere. If the selection of atmosphere is improper, there is obtained not a complex oxide of the $K_2MgF_4$-type structure but an oxide or oxide mixture having different structure. After sintering, the sample is quenched, if necessary, in liquid nitrogen or in ice water.

In synthesizing from carbonates, nitrates, or acetates, predetermined amounts of these salts are weighed out and treated at 500° to 1,200°C. in a manner similar to that in the case of oxides. When there is a large difference between the decomposition temperatures of the salts and the temperature of formation of the complex oxide, decomposition of the salts should be brought to completion by supplying air or oxygen during the decomposition. As compared with the method in which oxides are used as the starting materials, the present method is characterized by being capable of synthesizing the intended complex oxide at a lower temperature. The method has further advantages over the method utilizing oxides as the starting materials in that because of being operable as a wet process it is possible to obtain more uniform and more finely powdered complex oxide.

The method which makes use of alkaline metal carbonates as a flux is useful when it is desired to obtain a complex oxide which cannot be obtained by either of the aforesaid two methods. As the flux, it is preferred to use carbonate of alkaline metals such as lithium, potassium, and sodium, or mixtures thereof. For instance, $La_2NiO_4$ cannot be synthesized by either of the aforesaid two methods even in a controlled atmosphere unless an extremely high temperature and a long reaction time are used, and even when synthesized a single-phase $La_2NiO_4$ is difficult to obtain because of contamination with by-products. On the contrary, when a predetermined amount of a mixture of oxide components or a mixture of decomposition products of salts is thoroughly mixed with sodium carbonate in a ratio of 1 to 1 by weight and kept at a temperature above the melting point of sodium carbonate (i.e. 851° C.), for example, at 900° C. for 10 hours, the resulting product is identified as a single-phase $La_2NiO_4$, as analyzed by X-ray diffraction. The product thus obtained is a mixture of the alkaline metal carbonate and the intended complex oxide, and the latter in pure form is obtained by washing the product with water to remove the alkali metal carbonate.

The complex oxide synthesized by the aforesaid methods is used as a gas-sensor element in the form of shaped piece such as plate, rod, or disc; in the form of shaped piece of a mixture of the complex oxide and an inert oxide (e.g. alumina or silica), a metal, or a plastic; or in the form of film prepared by making the complex oxide or the said mixture into a slurry and coating the slurry on a base plate such as an alumina plate. It is needless to say that better performance characteristics of the sensor element are attained by making the form of a shaped piece so as to provide a large specific contact surface area against a sample gas. The term "specific contact surface area" as herein used means such a surface area of unit weight of the sensor material that contacts directly with the sample gas.

To enter into more detail, when it is intended to obtain a sensor element in the form of plate, rod, or disc, the complex oxide is shaped into a desired form and then sintered at 800° to 1,100°C. for 0.5 to several hours. When it is intended to obtain a coating in the form of a film on an alumina plate, silica glass, or other suitable base plates, the complex oxide is mixed with a binder such as, for example, a PVA (polyvinyl alcohole) solution, or a methylcellulose solution to form a slurry which is coated on a base plate and then sintered in a manner similar to that mentioned above. Further, the complex oxide can be supported on a porous carrier or mixed with an inert powder, and then sintered. The porosity of the element thus prepared is generally in the range of 60 to 70 percent.

When an air stream containing minute amounts of a oxidizable gaseous substance, such as, for example, an air stream containing about 0 to 2 mg/liter of ethyl alcohol, is allowed to contact with the above-said element while being heated at 100° to 500°C., the complex oxide manifests a catalytic action to effect oxidation of the oxidizable gaseous component. The catalytic action in this case is manifested through liberation of oxygen ions from the crystal, which is associated with a change in specific resistance of the complex oxide. This change in specific resistance permits detection of a oxidizable gaseous substance.

The change in specific resistance is correlated with the change in concentration of a oxidizable substance such as an alcohol. The change in resistance amounts to, for example, the order of several ten percent for an ethanol concentration of about 0.2 mg/liter, and also the response to the change in resistance is quick. The temperature coefficient of resistance is, for the most part, $2 \times 10^{-3}/°C$. or lower between room temperature and 800°C., and also S/N (signal to noise ratio) is so favorable as practically negligible.

Further, another important feature of the present sensor element is a rapid recovery of the resistance to the initial resistance when supply of a reducing gas is discontinued after the element has been contacted with said sample gas, and hence, the complex oxide may be utilized as such a gas sensor with good stability and reproducibility.

The above-said catalytic activity of the complex oxide may be explained presumably by the reactions (1) and (2) and the overall reaction (3):

$$R + Cat(O^*) \rightarrow nCO_2 + n'H_2O + Cat(V) \quad (1)$$
$$Cat(V) + \tfrac{1}{2}O_2 \rightarrow Cat(O^*) \quad (2)$$
$$R + mO_2 \rightarrow nCO_2 + n'H_2O \quad (3)$$

where R: oxidizable gas

Cat($O^*$): oxygen in the complex oxide crystal
Cat(V): oxygen vacancy in the complex oxide crystal
n, n', and m : coefficients.

When special attention is given to the oxygen in the complex oxide during oxidation reaction of an oxidizable gas represented by the reaction formulas (1), (2), and (3), it is presumable that the oxygen content varies in the following manner. Under the given conditions of temperature $T$ and oxygen partial pressure $Po_2$ at the temperature $T$, the complex oxide will assume such a $\delta$ value, i.e. $\delta o$, that the composition of the complex oxide may change into $$A_2BO_{4-\delta o} \quad \delta o = \delta o\,(T,\,Po_2) \quad (4)$$

corresponding to the oxygen partial pressure in the atmosphere in equilibrum with the complex oxide. When an oxidizable gas is supplied and the complex oxide acts as a catalyst, the composition changes in the following way:

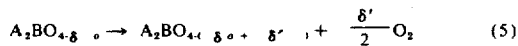

$$A_2BO_{4-\delta_0} \rightarrow A_2BO_{4-(\delta_0+\delta')} + \frac{\delta'}{2}O_2 \quad (5)$$

As compared with the composition when the complex oxide is not acting as a catalyst, the composition of the complex oxide catalyst assumes a larger $\delta$ value, i.e. $\delta_0 + \delta'$, which is determined by the ratio between each rate of the reactions (1) and (2).

The response characteristics of the sensor are determined by the overall effect of the two factors: the one is the change in nonstoichiometric parameter $\delta$ which is dependendent on equilibrium and the other is change of resistance in unit time, which is dependent on reaction kinetics. The former factor is given by the ratio between each rate of the catalytic reactions represented by (1) and (2). Since the activation energy of the reaction (2) is considered to be greater than that of the reaction (1), the rate of the reaction (2) increases rapidly with the increase in temperature. Consequently, as the temperature is increased, the change in $\delta$ becomes smaller and so the change of resistance becomes correspondingly smaller. The other factor becomes larger as the temperature is increased because the reaction rate increases with the temperature rise. As the overall result of these two competitive factors, there exists an optimum range of operating temperatures for the sensor.

An example of the change in specific resistance of the present sensor element in oxygen with the temperature is shown below. FIG. 2 is a plot of the results of measurement conducted on $Nd_{1.5}Sr_{0.5}NiO_4$ which has been shaped into a plate, about 35 mm in length, about 10 mm in width, and about 3 mm in thickness. The specific resistance of the element is deemed to be satisfactory enough, as compared with that of an ordinary semiconductor, which is 10 $\Omega$-cm or higher.

In FIG. 3 is shown the change in specific resistance of an element with the change in oxygen partial pressure, taking $La_{1.4}Sr_{0.6}NiO_4$. as an example. The element used is a plate shaped similarly to that used in FIG. 2. As is apparent from FIG. 3, it is seen that the specific resistance increases as the complex oxide becomes oxygen-deficient type.

The formula (5) has shown that $\delta$ becomes larger in the presence of an oxidizable gas than in its absence. From the results shown in FIG. 3, it is apparent that the increase in $\delta$ is accompanied with change in resistance of an element. This phenomenon suggests that a sensor element comprising the present complex oxide is useful for detecting an oxidizable gas in air. With respect to this point, more detailed description is given in the following Examples.

Example 1

A complex oxide, $La_{1.4}Sr_{0.6}NiO_4$, was coated on an alumina base-plate, 2 mm wide × 7 mm long, and then sintered to obtain an element.

Figure 4:
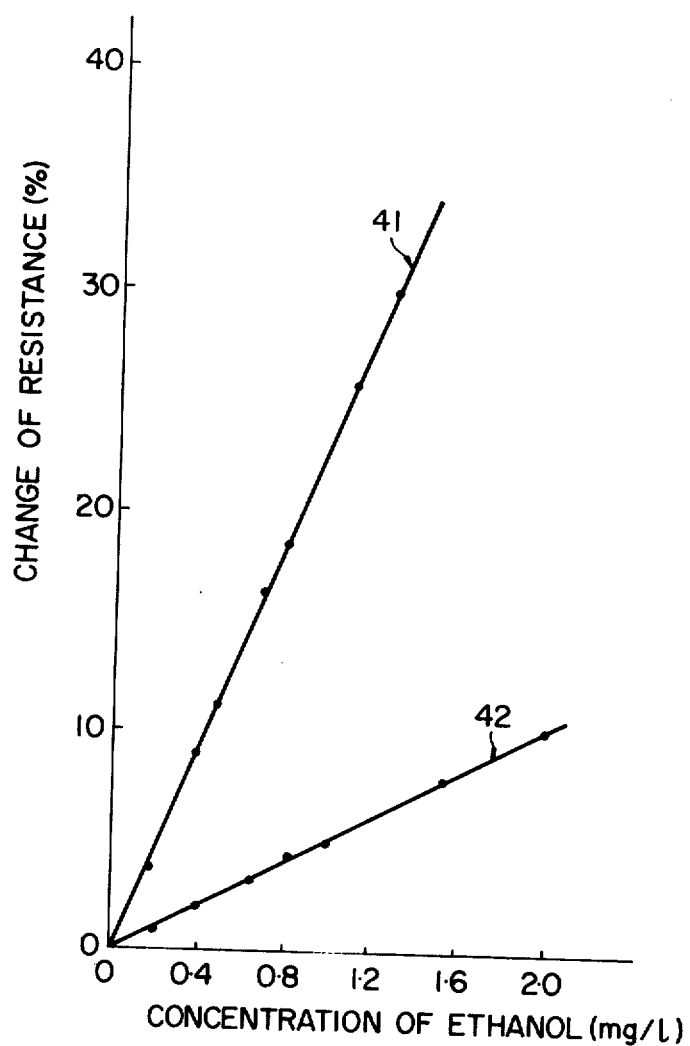
FIG. 4 is characteristic diagrams representing performance characteristics of a sensor element comprising $La_{1.4}Sr_{0.6}NiO_4$ when used for detecting ethanol.

In FIG. 4 are shown examples of the results of detecting ethanol. Straight lines 41 and 42 show the results when the temperatures of the sensor are 335°C. and 400°C., respectively. Although the element was of the same material, the resistance was different at these two temperatures, that is, 177 $\Omega$ and 135 $\Omega$, respectively. From FIG. 4, it is seen that a nearly perfect linear relationship exists between the change of resistance and the concentration of ethanol in the range from 0 to 2.0 mg/liter, and that the element comprising $La_{1.4}Sr_{0.6}NiO_4$ operates effectively at these temperatures as a quantitative sensor for ethanol. It is shown in the Figure that the change of resistance at 335°C. is four times as large as that at 400°C., indicating that there exists an optimum temperature range because of the aforesaid reason. As will be appreciated by those skilled in the art, changes in resistance are measured by apparatus. This apparatus will be referred to in the specification and claims as means for measuring the change in resistance of the material being referred to.

Example 2

Figure 5:
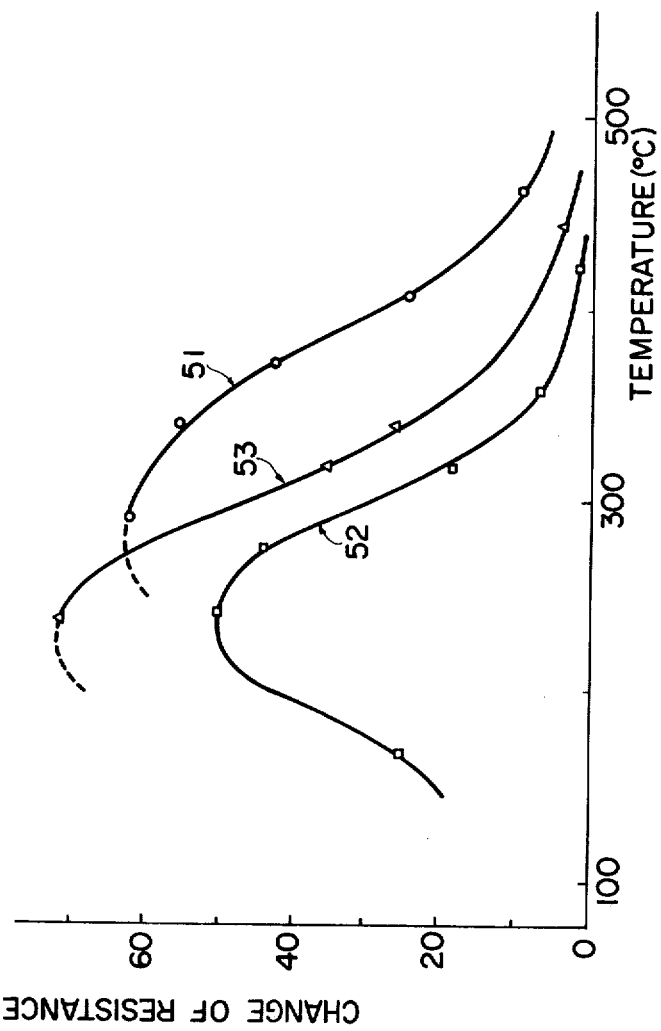
FIG. 5 is characteristic diagrams representing temperature dependency of the variation rate of specific resistance of sensor elements comprising $La_{2-x}Sr_xNiO_4$ when used for detecting ethanol.

By using $La_{2-x}Sr_xNiO_4$, elements of the similar shape to that in Example 1 were prepared. The temperature dependency of the variation rate of resistance of each element in detecting 0.8 mg/liter of ethanol was as shown in FIG. 5. The curves 51, 52, and 53 correspond to $x = 0.2, 0.6$, and 0.8, respectively. When $x$ is 0.2, the element showed a reliable response at temperatures above about 270°C., and the variation of resistance reached about 60 percent. When $x$ is 0.6, the element showed a reliable response at temperatures above about 150°C. and showed the maximum variation rate of resistance, i.e. 50 percent, at about 250°C. When $x$ is 0.8, the element showed a reliable response at temperatures above about 200°C. and the variation rate of resistance reached 70 percent or higher at temperatures around 240°C. These cases are examples which show that by varying the ratio between A and A' in the complex oxide represented by $A_{2-x}A'xBO_4$, it is possible to provide sensors having diversified characteristics and that it is possible to synthesize easily any composition which is most suitable for the use field and environment where the element is intended to be used.

As mentioned above, a complex oxide of the general formula, wherein $x$ is in the range $0 < x < 2$, is especially preferred because said complex oxide has an advantage in that a composition which meets the optimum conditions for use may be obtained.

Comparative Example 1

Figure 6:
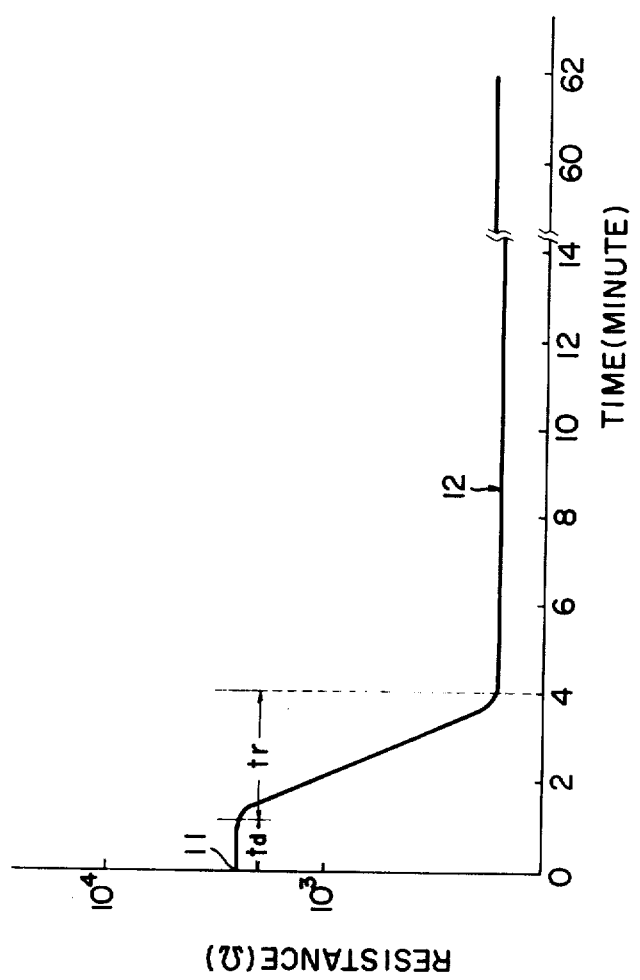
FIG. 6 is a response characteristics diagram of a conventional n-type tin oxide.

In FIG. 6 are shown the results obtained when a n-type tin oxide was used as the ethanol-sensing element. In the Figure, td represents a dead time from supply of ethanol to the start of response and $t_r$ the period of response. Supply of ethanol was started at the point 11 and discontinued at the point 12. The temperature was 170°C. As is seen from the Figure, with supply of ethanol the resistance decreases to a figure down about one place. However, the trouble in this case is that as is seen from the Figure, the initial resistance is not restored. Therefore, the element is entirely unsuitable for the repeated use at a constant temperature. In order to restore the resistance to the initial value, it is necessary to heat the element at a temperature of about 350°C. or higher. Although this seems to mean that when used at a temperature above 350°C., tin oxide can be used repeatedly for a long time, yet a tin oxide semiconductor is very unstable at a temperature above 350°C. and loses the gas-sensing capacity within 1 hour.

Example 3

Figure 7:
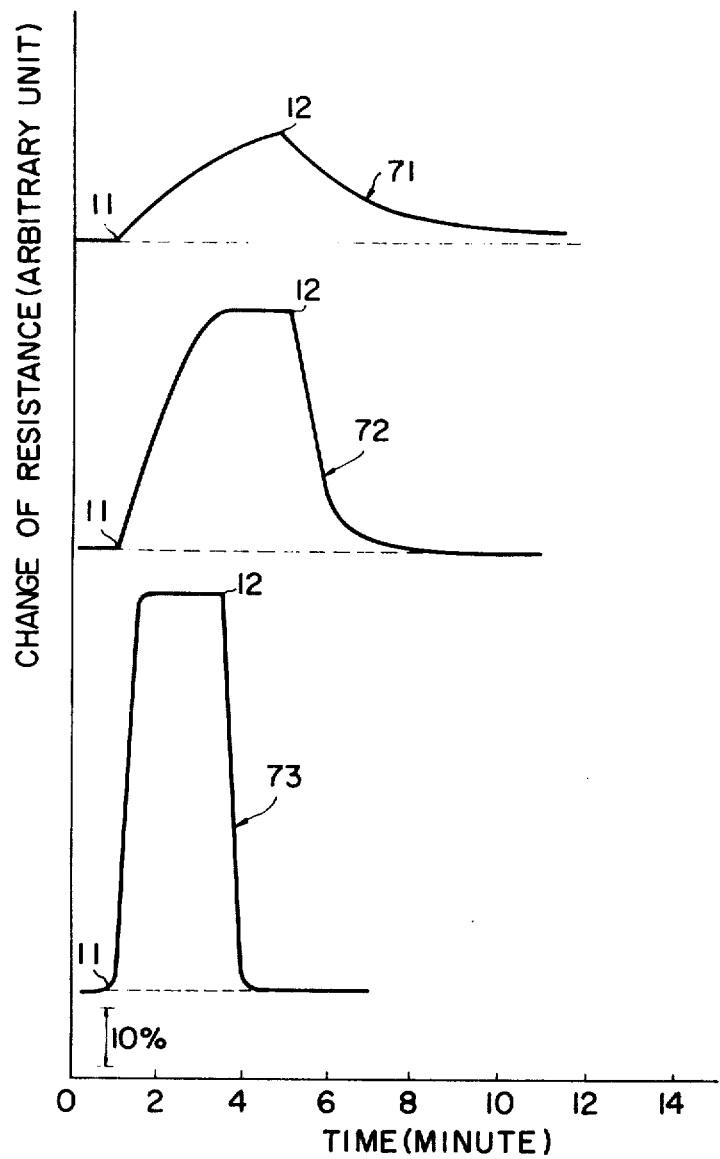
FIG. 7 is response characteristics diagrams of a sensor element comprising $La_{1.4}Sr_{0.6}NiO_4$.

By using various forms of the elements comprising $La_{1.4}Sr_{0.6}NiO_4$, their behavior in detecting ethanol were compared to obtain the results as shown in FIG. 7. The curves 71, 72, and 73 refer to a cylindrical element, 6 mm in diameter and 7 mm high, a cylindrical element, 3 mm in diameter and 5 mm high, and a film, 2 mm in width and 7 mm in length, coated on an alumina base plate, respectively. In the Figure, an ethanol-containing gas was supplied at the point 11, and the supply was discontinued at the point 12. From the Figure, it is seen that excellent response characteristics were manifested by an element in the form which provides a large specific contact surface against the gas so that a rapid reaction may take place. It is seen also from the Figure that a sensor more excellent in sensitivity and response characteristics may be prepared by optimizing the shape of the element.

Example 4

By using the same element as that in Example 1, various gaseous substances were detected to obtain the results as shown in Table 1. In the Table, (+) means that the resistance of the element was changed and (−) means that there was no change in the resistance. Number of (+) corresponds to the relative degree of change in the resistance. As is seen from the Table, the element of this invention also shows an excellent sensing performance against gaseous oxidizable substances other than ethanol.

Table 1

| Sample gas | Response performance of the sensor |
| --- | --- |
| Acetone | + + + |
| Ethanol | + + + |
| Methanol | + + + |
| Ether | + + + |
| Petroleum benzine | + + |
| Benzene | + |
| Toluene | + |
| Trichloroethylene | + + |
| Ammonia | − |
| Hydrogen peroxide | − |

Table 1-continued

| Sample gas | Response performance of the sensor |
| --- | --- |
| Water | − |
| Carbon monoxide | + + |

Examples 5 to 31

Elements in the form similar to that in Example 1 were prepared by using various complex oxides and tested for their performance for detecting ethanol. The results obtained were as shown in Table 2. The specific resistance was tested on test specimens in the form of plate, about 35 mm in length, about 10 mm in width, and about 3 mm in thickness.

Table 2

| EX. NO. | Complex oxide | Specific resistance ($\Omega$ cm) | Gas-detecting performance |
| --- | --- | --- | --- |
| 5 | $LiLaTiO_4$ | $2 \times 10^{-1}$ | ± |
| 6 | $LiDyTiO_4$ | $\sim 10^{-1}$ | ± |
| 7 | $LiLuTiO_4$ | $\sim 10^{-1}$ | ± |
| 8 | $LiyTiO_4$ | $8 \times 10^{-2}$ | + |
| 9 | $Sr_2CrO_4$ | $5 \times 10^{-1}$ | + |
| 10 | $SrLaCrO_4$ | $3 \times 10^{-2}$ | + + + |
| 11 | $SrMnO_4$ | $2 \times 10^{-1}$ | + + |
| 12 | $Ga_2MnO_4$ | $6 \times 10^{-2}$ | + + |
| 13 | $NdCaMnC_4$ | $7 \times 10^{-3}$ | + + + |
| 14 | $Ba_2MnO_4$ | $8 \times 10^{-2}$ | + + + |
| 15 | $SrLaMnO_4$ | $3 \times 10^{-3}$ | + + + |
| 16 | $SrFeCoO_4$ | $10^2 \sim 10^{-1}$ | + + |
| 17 | $SrLaFe_{0.5}Co_{0.5}O_4$ | $2.5 \times 10^{-2}$ | + + + |
| 18 | $SrLaFeO_4$ | $6 \times 10^{-2}$ | + + + |
| 19 | $SrLaCoO_4$ | $2 \times 10^{-3}$ | + + + |
| 20 | $La_2Co_{0.5}Ni_{0.5}O_4$ | $7 \times 10^{-1}$ | + + + + |
| 21 | $Sr_{1.5}La_{0.5}Co_{0.5}Ti_{0.5}O_4$ | $1.9 \times 10^0$ | + + |
| 22 | $La_2NiO_4$ | $4 \times 10^{-2}$ | + + + + |
| 23 | $Pr_2NiO_4$ | $9 \times 10^{-2}$ | + + + |
| 24 | $Nd_2NiO_4$ | $6 \times 10^{-2}$ | + + + |
| 25 | $LaSrNiO_4$ | $5.4 \times 10^{-8}$ | + + + + |
| 26 | $Pr_2CuO_4$ | $\sim 10^0$ | + |
| 27 | $Sm_2CuO_4$ | $\sim 10^0$ | + + |
| 28 | $Eu_2CuO_4$ | $\sim 10^1$ | + + |
| 29 | $Gd_2CuO_4$ | $10^1$ | + + |
| 30 | $La_{1.8}Hf_{0.2}CoO_4$ | $\sim 10^1$ | + + + |
| 31 | $La_{0.25}Nd_{0.75}Sr_{0.4}Ba_{0.1}CoO_4$ | $10^{-3}$ | + + + + |

As is seen from Table 2, the complex oxide containing at least lanthanum as A or at least nickel as B has an advantage of excellent sensitivity.

As stated in the foregoing, the gas-sensor element of this invention is distinguished in detecting performance for oxidizable gas. Examples of most suitable applications of the element include an automatic on-off control device for a ventilating fan by means of detecting carbon monoxide in the living-environmental atmosphere, a fire and smoke alarm by means of detecting carbon monoxide and smoke, a flame sensor for use in a flue, a sensor for carbon monoxide or nitrogen oxides in various oxidizable pollutant gases in the atmosphere, an automatic ventilation system by detecting hazardous gases in the tunnel, a sensor for estimating concentration of ethanol in the breath of an individual who has taken an alcoholic beverage, etc.

We claim:

1. In a method for detecting the presence of a gaseous substance in a test gas comprising contacting the test gas with a sensor element whose resistance changes in the presence of said gaseous substance and measuring the resistance of said sensing element while said test gas is in contact therewith, the improvement wherein said gaseous substance is an oxidizable gas and further wherein said sensing element comprises a complex metal oxide having a perovskite-type crystal structure and represented by the general formula $A_{2-x}A'_xBO_{4-\delta}$, wherein A is at least one element selected from the group consisting of rare earth elements of the atomic numbers from 57 to 71, yttrium, and hafnium, A' is at least one alkaline earth metal, B is at least one element selected from the group consisting of transition metals of the atomic numbers from 21 to 30, O is oxygen, $x$ is in the range of $0 \leq x \leq 2$, and $\delta$ is a nonstoichiometric parameter.

2. A method according to claim 1, wherein the complex metal oxide contains at least nickel as B in the general formula.

3. A method according to claim 1, wherein the oxidizable gas is vapor of an alcohol.

4. A method according to claim 1, wherein said oxidizable gas is allowed to come into contact with said sensing element at a temperature of about 100° to about 500° C.

5. A method according to claim 1, wherein the complex metal oxide represented by the general formula $A_{2-x}A'_xBO_{4-\delta}$ contains at least lanthanum as A.

6. A method according to claim 5, wherein the complex metal oxide contains at least strontium as A' in the general formula.

7. A method according to claim 6, wherein the complex metal oxide contains at least nickel as B in the general formula.

8. A method for according to claim 1, wherein x in the general formula $A_{2-x}A'_xBO_{4-\delta}$ is in the range of $0 < x < 2$.

9. A method according to claim 8, wherein the complex metal oxide contains at least lanthanum as A in the general formula.

10. A method according to claim 8, wherein the complex metal oxide contains at least nickel as B in the general formula.

11. A method according to claim 8, wherein the oxidizable gas is vapor of an alcohol.

12. A method according to claim 1, wherein detecting of the oxidizable gas is carried out by measuring the change in specific resistance of said complex metal oxide.

13. A method according to claim 12, wherein x in the general formula $A_{2-x}A'_xBO_{4-\delta}$ is in the range of $0 < x < 2$.

14. A method according to claim 12, wherein the complex metal oxide represented by the general formula $A_{2-x}A'_xBO_{4-\delta}$ contains at least lanthanum as A.

15. A method according to claim 12, wherein the complex metal oxide contains at least strontium as A' in the general formula.

16. A method according to claim 12, wherein the complex metal oxide contains at least nickel as B in the general formula.

17. A method according to claim 12, wherein the oxidizable gas is vapor of an alcohol.

18. A method according to claim 12, wherein said oxidizable gas is allowed to come into contact with said sensing element at a temperature of about 100° to about 500° C.

19. A method according to claim 1, wherein detecting of the oxidizable gas is carried out by measuring the change in specific resistance of said complex metal oxide when the oxidizable gas contacting said metal oxide is oxidized or decomposed by catalytic action of said metal oxide.

20. A method according to claim 19, wherein x in the general formula $A_{2-x}A'_xBO_{4-\delta}$ is in the range of $0 < x < 2$.

21. A method according to claim 19, wherein the complex metal oxide represented by the general formula $A_{2-x}A'_xBO_{4-\delta}$ contains at least lanthanum as A.

22. A method according to claim 19, wherein the complex metal oxide contains at least strontium as A' in the general formula.

23. A method according to claim 19, wherein the complex metal oxide contains at least nickel as B in the general formula.

24. A method according to claim 19, wherein the oxidizable gas is vapor of an alcohol.

25. A method according to claim 19, wherein said oxidizable gas is allowed to come into contact with said sensing element at a temperature of about 100° to about 500° C.

26. In a gas sensor for detecting the presence of an oxidizable gas in a test gas, said gas sensor including a sensing element whose resistance changes in the presence of the gas to be detected, said sensing element including a surface capable of coming into contact with said test gas and means for indicating the presence of said oxidizable gas in said test gas in response to a change in resistance of said sensing element, the improvement wherein said sensing element comprises a complex metal oxide having a $K_2MgF_4$-type crystal structure and represented by the general formula $A_{2-x}A'_xBO_{4-\delta}$, wherein A is at least one element selected from the group consisting of rare earth elements of the atomic numbers from 57 to 71, yttrium, and hafnium, A' is at least one alkaline earth metal, B is at least one element selected from the group consisting of transition elements of the atomic numbers 21 to 30, O is oxygen, x is in the range of $0 \leq x \leq 2$, and $\delta$ is a nonstoichiometric parameter.

27. A gas-sensor according to claim 26, wherein the complex metal oxide contains at least nickel as B in the general formula.

28. A gas-sensor according to claim 26, wherein the oxidizable gas is vapor of an alcohol.

29. A gas sensor according to claim 26, further including means for maintaining said sensor element at a constant temperature between about 100° and 500° C.

30. The gas sensor of claim 26, wherein said sensing element is in the form of a plate, rod or disc.

31. The gas sensor of claim 26, wherein said complex metal oxide is a coating on a substrate.

32. A gas-sensor according to claim 26, wherein the complex metal oxide represented by the general formula $A_{2-x}A'_xBO_{4-\delta}$ contains at least lanthanum as A.

33. A gas-sensor according to claim 32, wherein the complex metal oxide contains at least strontium as A' in the general formula.

34. A gas-sensor according to claim 33, wherein the complex metal oxide contains at least nickel as B in the general formula.

35. A gas-sensor according to claim 26, wherein x in the general formula $A_{2-x}A'_xBO_{4-\delta}$ is in the range of $0 < x < 2$.

36. A gas-sensor according to claim 35, wherein the complex metal oxide contains at least lanthanum as A in the general formula.

37. A gas-sensor according to claim 35, wherein the complex metal oxide contains at least nickel as B in the general formula.

38. A gas-sensor according to claim 35, wherein the oxidizable gas is vapor of an alcohol.

* * * * *